United States Patent
Wilson et al.

(10) Patent No.: US 11,109,766 B2
(45) Date of Patent: Sep. 7, 2021

(54) FLUID FLOW MEASUREMENT SYSTEMS AND METHODS

(71) Applicant: ACIST Medical Systems, Inc., Eden Prairie, MN (US)

(72) Inventors: Robert F. Wilson, Shoreview, MN (US); Edward R. Miller, Eden Prairie, MN (US); Sidney Donald Nystrom, Shoreview, MN (US); Kendall R. Waters, Livermore, CA (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 39 days.

(21) Appl. No.: 13/902,224

(22) Filed: May 24, 2013

(65) Prior Publication Data
US 2013/0317359 A1 Nov. 28, 2013

Related U.S. Application Data

(60) Provisional application No. 61/651,972, filed on May 25, 2012, provisional application No. 61/651,930, filed on May 25, 2012.

(51) Int. Cl.
*A61B 5/027* (2006.01)
*A61B 8/06* (2006.01)
(Continued)

(52) U.S. Cl.
CPC .......... *A61B 5/0205* (2013.01); *A61B 5/0066* (2013.01); *A61B 5/0084* (2013.01);
(Continued)

(58) Field of Classification Search
None
See application file for complete search history.

(56) References Cited

U.S. PATENT DOCUMENTS

| 2,627,270 A | 2/1953 | Glass |
| 4,044,757 A | 8/1977 | McWhorter et al. |

(Continued)

FOREIGN PATENT DOCUMENTS

| CN | 87202114 U | 4/1988 |
| CN | 1617686 A | 5/2005 |

(Continued)

OTHER PUBLICATIONS

International Searching Authority, Notification of Transmittal of the International Search Report and the Written Opinion of the International Searching Authority, or the Declaration, (co-pending) International Application No. PCT/US2013/042676; dated Aug. 30, 2013, 14 pages, European Patent Office, Rijswijk, The Netherlands.

(Continued)

*Primary Examiner* — Oommen Jacob
*Assistant Examiner* — Shahdeep Mohammed
(74) *Attorney, Agent, or Firm* — Fredrikson & Byron, P.A.

(57) ABSTRACT

This disclosure provides systems and methods for measuring fluid flow in a vasculature system of a patient. Some systems may include an injection system configured to inject a bolus of fluid into a vessel of a patient. Some systems may include a measurement engine configured to monitor the bolus of fluid in the vessel using measurement data generated by an intravascular measuring device. The measurement engine may determine a travel distance of the bolus of fluid and an elapsed time during which the bolus of fluid traversed the travel distance based on the measurement data. A fluid flow rate (e.g., velocity, volumetric flow) of the vessel may be calculated using the travel distance and the elapsed time.

28 Claims, 7 Drawing Sheets

(51) Int. Cl.

| | | |
|---|---|---|
| *A61B 8/12* | (2006.01) | |
| *A61B 8/08* | (2006.01) | |
| *A61B 5/026* | (2006.01) | |
| *A61B 5/107* | (2006.01) | |
| *A61B 5/00* | (2006.01) | |
| *A61B 8/00* | (2006.01) | |
| *A61M 5/00* | (2006.01) | |
| *A61B 5/0205* | (2006.01) | |
| *A61B 5/0275* | (2006.01) | |
| *A61M 5/142* | (2006.01) | |
| *A61M 5/168* | (2006.01) | |

(52) U.S. Cl.
CPC .............. *A61B 5/026* (2013.01); *A61B 5/027* (2013.01); *A61B 5/0261* (2013.01); *A61B 5/0275* (2013.01); *A61B 5/1076* (2013.01); *A61B 8/06* (2013.01); *A61B 8/12* (2013.01); *A61B 8/445* (2013.01); *A61B 8/5223* (2013.01); *A61M 5/142* (2013.01); *A61M 5/16831* (2013.01); *A61M 5/007* (2013.01); *A61M 2205/3375* (2013.01)

(56) References Cited

U.S. PATENT DOCUMENTS

| | | | |
|---|---|---|---|
| 4,084,606 | A | 4/1978 | Mittleman |
| 4,462,409 | A | 7/1984 | Pace et al. |
| 4,819,684 | A | 4/1989 | Zaugg et al. |
| 5,097,841 | A | 3/1992 | Moriuchi et al. |
| 5,098,405 | A | 3/1992 | Peterson et al. |
| 5,176,658 | A | 1/1993 | Ranford |
| 5,190,067 | A | 3/1993 | Paradis et al. |
| 5,267,964 | A | 12/1993 | Karg |
| 5,573,515 | A | 11/1996 | Wilson et al. |
| 5,800,397 | A | 9/1998 | Wilson et al. |
| 5,843,044 | A | 12/1998 | Moorehead |
| 5,882,343 | A | 3/1999 | Wilson et al. |
| 6,050,450 | A | 4/2000 | Gardos |
| 6,099,502 | A | 8/2000 | Duchon et al. |
| 6,182,698 | B1 | 2/2001 | Barak |
| 6,221,045 | B1 | 4/2001 | Duchon et al. |
| 6,254,835 | B1 | 7/2001 | Feygin |
| 6,344,030 | B1 | 2/2002 | Duchon et al. |
| 6,447,481 | B1 | 9/2002 | Duchon et al. |
| 6,569,117 | B1 | 5/2003 | Ziv et al. |
| 6,638,258 | B2 | 10/2003 | Schwartz et al. |
| 6,656,157 | B1 | 12/2003 | Duchon et al. |
| 6,708,714 | B1 | 3/2004 | Mijers |
| 6,733,477 | B2 | 5/2004 | Cowan et al. |
| 6,746,427 | B2 | 6/2004 | Duchon et al. |
| 6,752,789 | B2 | 6/2004 | Duchon et al. |
| 6,945,959 | B2 | 9/2005 | Duchon et al. |
| 7,094,216 | B2 | 8/2006 | Trombley, III et al. |
| 7,128,729 | B2 | 10/2006 | Duchon et al. |
| 7,153,288 | B2 | 12/2006 | Duchon et al. |
| 7,267,666 | B1 | 9/2007 | Duchon et al. |
| 7,326,186 | B2 | 2/2008 | Trombley, III et al. |
| 7,357,785 | B2 | 4/2008 | Duchon et al. |
| 7,389,788 | B2 | 6/2008 | Wilson et al. |
| 7,566,326 | B2 | 7/2009 | Duchon et al. |
| 7,581,559 | B2 | 9/2009 | Bausmith, III |
| 7,610,936 | B2 | 11/2009 | Spohn et al. |
| 7,617,837 | B2 | 11/2009 | Wilson et al. |
| 7,662,124 | B2 | 2/2010 | Duchon et al. |
| 7,703,483 | B2 | 4/2010 | Hartman et al. |
| 8,412,312 | B2 | 4/2013 | Judell et al. |
| 2002/0065467 | A1* | 5/2002 | Schutt ........................ 600/454 |
| 2002/0103437 | A1* | 8/2002 | Jibiki ........................ 600/454 |
| 2003/0122095 | A1 | 7/2003 | Wilson et al. |
| 2005/0230575 | A1 | 10/2005 | Zelenski et al. |
| 2005/0234407 | A1 | 10/2005 | Spohn et al. |
| 2005/0234428 | A1 | 10/2005 | Spohn et al. |
| 2006/0079768 | A1 | 4/2006 | Small et al. |
| 2006/0167415 | A1 | 7/2006 | Nemoto |
| 2006/0178632 | A1 | 8/2006 | Trombley et al. |
| 2006/0180202 | A1 | 8/2006 | Wilson et al. |
| 2006/0184122 | A1* | 8/2006 | Nemoto ........................ 604/154 |
| 2007/0055202 | A1 | 3/2007 | Duchon et al. |
| 2007/0161970 | A1 | 7/2007 | Spohn et al. |
| 2007/0167919 | A1 | 7/2007 | Nemoto et al. |
| 2007/0179487 | A1 | 8/2007 | Tearney et al. |
| 2007/0244435 | A1 | 10/2007 | Hicks |
| 2007/0249936 | A1* | 10/2007 | Deckman et al. ............. 600/439 |
| 2008/0086087 | A1 | 4/2008 | Spohn et al. |
| 2008/0091142 | A1 | 4/2008 | Trombley et al. |
| 2008/0103437 | A1 | 5/2008 | Duchon et al. |
| 2008/0161634 | A1 | 7/2008 | Nemoto et al. |
| 2008/0183131 | A1 | 7/2008 | Duchon et al. |
| 2008/0300483 | A1 | 12/2008 | Nemoto et al. |
| 2009/0131765 | A1* | 5/2009 | Roschak et al. ............... 600/301 |
| 2009/0149743 | A1 | 6/2009 | Barron et al. |
| 2009/0221914 | A1 | 9/2009 | Barrett et al. |
| 2009/0234231 | A1 | 9/2009 | Knight et al. |
| 2009/0304593 | A1* | 12/2009 | Frinking et al. ............... 424/9.1 |
| 2009/0312740 | A1 | 12/2009 | Kim et al. |
| 2010/0019178 | A1 | 1/2010 | Wilson et al. |
| 2010/0094133 | A1* | 4/2010 | Yoshiara et al. .............. 600/453 |
| 2010/0113924 | A1 | 5/2010 | Hajicek et al. |
| 2010/0249588 | A1 | 9/2010 | Knight |
| 2011/0071404 | A1 | 3/2011 | Schmitt et al. |
| 2011/0071405 | A1* | 3/2011 | Judell .................. A61B 5/0066 600/479 |
| 2011/0077528 | A1 | 3/2011 | Kemp et al. |
| 2011/0196255 | A1* | 8/2011 | Kassab ............... A61B 5/02007 600/549 |
| 2012/0022360 | A1* | 1/2012 | Kemp .................. A61B 5/6852 600/410 |
| 2013/0216114 | A1* | 8/2013 | Courtney ............. A61B 5/6852 382/130 |
| 2014/0121513 | A1* | 5/2014 | Tolkowsky ........ A61B 5/02007 600/431 |
| 2014/0180083 | A1 | 6/2014 | Hoseit |

FOREIGN PATENT DOCUMENTS

| | | |
|---|---|---|
| CN | 101039711 A | 9/2007 |
| CN | 101355975 A | 1/2009 |
| EP | 0331526 A1 | 9/1989 |
| JP | S62-221335 A | 9/1987 |
| JP | 2001178720 A | 7/2001 |
| JP | 2001245862 A | 9/2001 |
| JP | 2002210007 A | 7/2002 |
| WO | 02064195 A2 | 8/2002 |
| WO | 03050491 A2 | 6/2003 |
| WO | 2005070299 A1 | 8/2005 |
| WO | 2005110007 A2 | 11/2005 |
| WO | 2007062315 A2 | 5/2007 |

OTHER PUBLICATIONS

Wagner, Robert F., "Statistics of Speckle in Ultrasound B-Scans", IEEE Transactions on Sonics and Ultrsonics, vol. 30, No. 3, May 1983.

Shira, Yan Chen et al., "Phase Insensitive Homomorphic Image Processing for Speckle Reduction", Ultrasonic Imaging vol. 18, 122-139 (1996), Article No. 0007. Copyright 1996 by Academic Press, Inc. (0161-7346/96).

Lupotti Fa, et al., "Quantitative IVUS Blood Flow Using an Array Catheter", Computers in Cardiology 2001; 28:5-8.

Webster, John G., "Measurement of Flow and Volume of Blood", Medical Instrumentation Application and Design, Wiley, 4th Edition, 2009, pp. 341-342. (ISBN: 0471676004, 9780471676003).

Ledoux, Leon A.F., et al., "Angle-Independent Motion Measurement by Correlation of Ultrasound Signals Assessed with a Single Circular-Shaped Transducer," Ultrasonic Imaging 21, 216-240 (1999).

Wilson, L.S., et al., "Measurement of Two-Dimensional Blood Velocity Vectors by the Ultrasonic Speckle Projection Technique," Ultrasonic Imaging 15, 286-303 (1993).

(56) References Cited

OTHER PUBLICATIONS

Xu, Tiantian, "Two-Dimensional Blood Flow Velocity Estimation Using Ultrasound Speckle Pattern Dependence on Scan Direction and Velocity," Aug. 1, 2012, 169 pages.

Wang, L. M. et al., "Contrast Medium Assisted Fluid Flow Measurements", IEEE Transactions on Ultrasonics, Ferroelectric, and Frequency Control, Mar. 1995, pp. 309-315, vol. 42, No. 2, Champagne, Illinois.

Bazilevs, Yuri et al., "From Imaging to Prediction: Emerging Non-Invasive Methods in Pediatric Cardiology", Progress in Pediatric Cardiology, Dec. 2010, pp. 81-89, vol. 30, No. 1-2, Amsterdam, The Netherlands.

Written Opinion of the International Preliminary Examining Authority, (co-pending) International Application No. PCT/US2013/042676, 8 pages, European Patent Office, Rijswijk, The Netherlands, dated Aug. 30, 2013.

Chapter II Demand and Response to Written Opinion dated Aug. 13, 2014 for PCT/US2013/042676, 22 pages, sent International Preliminary Examining Authority, European Patent Office, Rijswijk, The Netherlands dated Oct. 13, 2014.

Chapter II Demand and Response to Written Opinion dated Aug. 30, 2013 for PCT/US2013/042676, 26 pages, sent to International Preliminary Examining Authority, European Patent Office, Rijswijk, The Netherlands dated Mar. 25, 2014.

Notification of Transmittal of the International Preliminary Report on Patentability for PCT/US2013/042676, dated Nov. 4, 2014, 12 pages, International Preliminary Examining Authority, European Patent Office Rijswijk, The Netherlands.

Written Opinion for PCT/US2013/042676, dated Aug. 13, 2014, 8 pages, International Preliminary Examining Authority, European Patent Office, Rijswijk, The Netherlands.

Notification of Transmittal of the International Search Report and the Written Opinion of the International Searching Authority, or the Declaration for PCT/US2014/046374, dated Mar. 27, 2015, 13 pages, International Searching Authority, European Patent Office Rijswijk, The Netherlands.

Revell et al., "Computer Vision Elastography: Speckle Adaptive Motion Estimation for Elastography Using Ultrasound Sequences," IEEE Transactions on Medical Imaging, vol. 24, No. 6, Jun. 1, 2005, pp. 755-766.

* cited by examiner

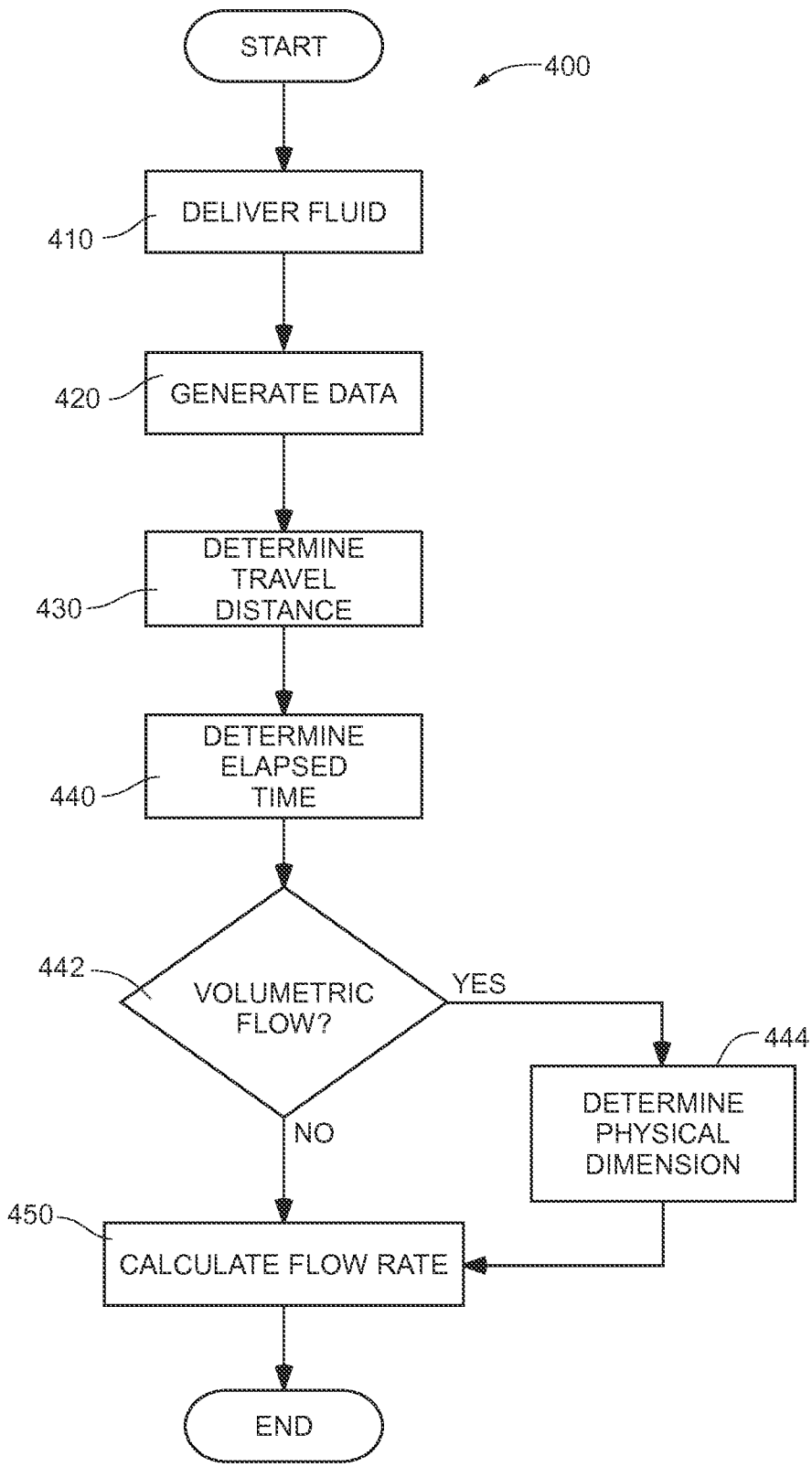

FLUID FLOW MEASUREMENT SYSTEMS AND METHODS

RELATED APPLICATIONS

This application claims priority to provisional application U.S. Ser. No. 61/651,972 filed May 25, 2012 and provisional application U.S. Ser. No. 61/651,930 filed May 25, 2012, the disclosures of which are herein incorporated by reference in their entirety.

BACKGROUND

Diagnostic value is attributed to understanding the fluid flow within a patient's vasculature as it may help identify and locate blockages in a vessel of the patient. Thermodilution is one method that may be used to determine fluid flow through a vessel of a patient and is commonly performed using a Swan-Ganz catheter, also known as a pulmonary artery catheter, which is used exclusively in the heart. Thermodilution determines cardiac output of the heart by introducing a heated or cooled fluid into the heart and then measuring a change in temperature downstream. A cardiac output is determined based on the measured change in temperature. Other methods for determining fluid flow within a vessel include Doppler techniques, which use ultrasound and the Doppler effect to determine velocity of blood through a vessel. Doppler techniques, however, are susceptible to error induced by backflow or other turbulent velocity fluctuations that may occur in a vasculature of a patient. Fluid flow through a vessel may also be estimated using fractional flow reserve (FFR) techniques. FFR techniques typically estimate fluid flow by measuring pressure across a lesion in a vessel. FFR techniques do not measure fluid flow through the vessel, but rather approximate/estimate the flow rate as FFR measurements are performed during hyperemia (e.g., drug induced dilation of the blood vessels).

IVUS involves one or more ultrasound transducers emitting ultrasound energy based on received electrical signals and sending return electrical signals based on ultrasound energy reflected by various intravascular structures. IVUS is often used to generate images. In some instances, a console with a high-resolution display is able to display IVUS images in real-time. In this way, IVUS can be used to provide in-vivo visualization of the vascular structures and lumens, including the coronary artery lumen, coronary artery wall morphology, and devices, such as stents, at or near the surface of the coronary artery wall. IVUS imaging may be used to visualize diseased vessels, including coronary artery disease. In some instances, the ultrasound transducer(s) can operate at a relatively high frequency (e.g., 10 MHz-60 MHz, in some preferred embodiments, 40 MHz-60 MHz) and can be carried near a distal end of an IVUS catheter. Some IVUS systems involve mechanically rotating the IVUS catheter for 360-degree visualization.

With the advent of higher frequency IVUS imaging systems as well as optical coherence tomography (OCT) systems, the precision of the image of the vessel is significantly improved when blood is displaced from the lumen of the vessel. Accordingly, imaging systems may include an injection system configured to deliver a flushing agent into the vessel before the vessel is imaged.

SUMMARY

This disclosure generally relates to systems and methods that may be used to measure fluid flow through a vessel using imaging techniques. In certain examples, a measurement system employing intravascular ultrasound (IVUS), optical coherence tomography (OCT), or other suitable imaging technique may be used to determine fluid flow through a vessel. In one example, an injector system of a measurement system may deliver a bolus of a flushing agent into a vessel of a patient and the bolus may be observed using, for example, an ultrasound transducer. Data collected from the ultrasound transducer may be used to determine a travel distance of the bolus within the vessel and/or an elapsed time during which the bolus traveled the distance. The flow rate of the vessel may then be determined based on the travel distance and the elapsed time during which the bolus traveled. In some examples, the travel distance may be derived where a cross-sectional area of the vessel and the volume of the bolus are known or calculated.

Examples disclosed in this disclosure may provide one or more advantages over existing systems and methods to determine flow rate within a vasculature of a patient. For example, fluid flow may be measured in any vessel large enough to accommodate an imaging catheter (e.g., an IVUS or OCT catheter). Further, some examples actually measure fluid flow by observing a rate of travel of a bolus in a vessel as compared to systems and methods that provide an approximation or prediction of fluid flow. Also, fluid flow measurements in some examples may be performed using commercially available imaging systems providing the advantage of performing fluid flow measurements during intravascular imaging operations as compared to non-procedure related methods to measure and calculate fluid flow. Moreover, the ability to measure fluid flow during an imaging operation decreases diagnosis time as potential issues requiring fluid flow measurements may be immediately performed without having to schedule another procedure or using additional equipment. Accordingly, cost savings and time savings may be enjoyed by patients and care providers.

The details of one or more examples are set forth in the accompanying drawings and the description below. Other features, objects, and advantages will be apparent from the description and drawings, and from the claims.

BRIEF DESCRIPTION OF DRAWINGS

FIG. 4 is a flow diagram illustrating a method for determining a flow rate through a vessel of a patient.

DETAILED DESCRIPTION

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Figure 1:
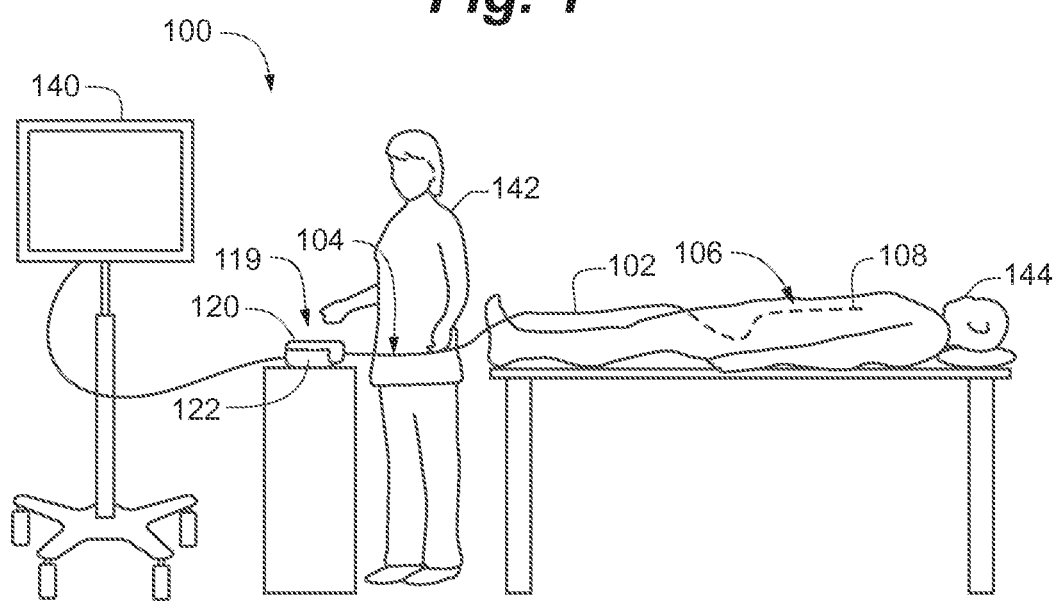
FIG. 1 is an illustrative system configured to perform hemodynamic measurements.

FIG. 1 is an illustrative example of a system 100 that may be configured to perform hemodynamic measurements, for example fluid flow within a vasculature of a patient. System 100 may include a catheter assembly 102 having a proximal end 104 and a distal end 106 configured to be inserted into a vessel of a patient 144. In one example, catheter assembly 102 may be inserted into patient 144 via the femoral artery and guided to an area of interest within the patient 144. The broken lines in FIG. 1 represent portions of catheter assembly 102 within the patient 144. In some examples, catheter assembly 102 may include an intravascular measuring device 108 having a measurement module within distal end 106 configured to emit and receive wave-based energy and generate measurement data—e.g., to image the area of interest within the patient 144. For example, where system 100 is an IVUS system, intravascular measuring device 108 may comprise an IVUS imaging probe including an ultrasound transducer configured to emit and receive ultrasound sound energy and generate ultrasound data. In another example, system 100 may be an OCT system wherein the intravascular measuring device may comprise an OCT imaging probe including a measurement module configured to emit and receive light and generate OCT data.

System 100 may include a translation mechanism 119, which may comprise a patient interface module (PIM) 120 and a linear translation system (LTS) 122. As is discussed further below, LTS 122 may be mechanically engaged with catheter assembly 102 and configured to translate the catheter assembly 102 a controlled distance within the patient 144 during a translation operation, for example a pullback or push-forward operation. In this example, PIM 120 of the translation mechanism 119 can act as an interface with the catheter assembly 102.

A computing machine 140 of system 100 may comprise one or more processors configured to receive commands from a system user 142 and/or display data acquired from catheter assembly 102 via a user interface. In one example, the computing machine may be a personal computer including computer peripherals (e.g., keyboard, mouse, electronic display) to receive inputs from the system user 142 and output system information and/or signals received from catheter assembly 102 (e.g., rendered images). In some examples, the user interface of the computing machine may be a touchscreen display configured to act as both an input device and an output device. In some examples, computing machine 140 may include memory modules for storing instructions, or software, executable by the one or more processors. For example, computing machine 140 may include software such that the computing machine 140 operates as a measurement engine for measuring fluid flow within the vasculature of a patient.

Figure 2:
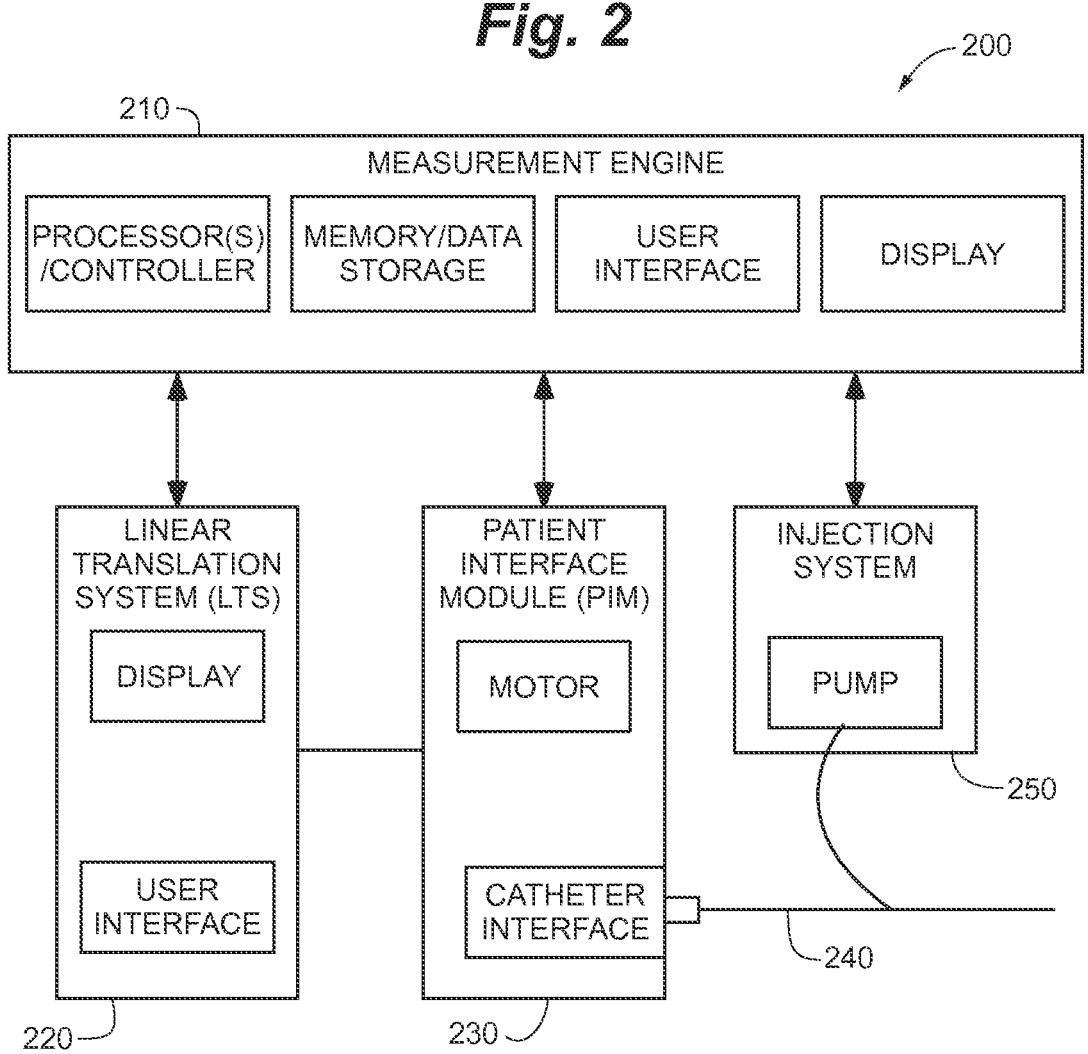
FIG. 2 is a block diagram of an illustrative IVUS system configured to perform hemodynamic measurements.

FIG. 2 is a high-level block diagram of an example of an IVUS system 200 that may be used to perform hemodynamic measurements. IVUS system 200 can include a measurement engine 210, a PIM 230, a LTS 220, and a catheter assembly 240. Measurement engine 210 can be the central component of the IVUS system 200 and may perform one or more functions including, for example, hemodynamic calculations, image generation, display of IVUS images and other information, control of the system components, storing and exporting the image data, a user interface (e.g., GUI) for operating the system, analysis tools (e.g., area measurements, linear measurements, and annotations), and so on. In some examples, measurement engine may be a computing machine comprising one or more programmable processors. In some examples, measurement engine may comprise one or more memory modules including instructions that may be executed by one or more programmable processors (e.g., software).

PIM 230 can provide the electromechanical interface between catheter assembly 240 and measurement engine 210. In some embodiments, PIM 230 can provide the mechanical interface to secure catheter assembly 240, as well as the mechanical energy to rotate an imaging assembly of catheter assembly 240. In some embodiments, PIM 230 can provide the electrical interface that transmits signals from an integrated ultrasound generator to catheter assembly 240 and receives return signals.

The catheter assembly 240 may be a minimally invasive intravascular ultrasound imaging catheter. The catheter assembly 240 can emit ultrasound energy from a transducer at its distal tip, which may be guided into an area of interest of a patient, for example the coronary arteries of the heart. Ultrasound waves that are reflected from vascular tissues can be received by the transducer and sent through PIM 230 to measurement engine 210. The catheter assembly 240 may be operated at selected frequencies, such as 40 MHz or 60 MHz, depending on user preference or a specific application. In some embodiments, catheter assembly 240 can include a drive cable surrounded by a sheath. In some such embodiments, the proximal end of catheter assembly 240 can connect to PIM 230 and can be mechanically rotated by PIM 230. In some embodiments, the distal end of catheter assembly 240 may include an intravascular measuring device having an imaging element connected to and rotated through 360 degrees by the drive cable. The imaging element may be a broadband ultrasound transducer that emits and receives ultrasound energy between, for example, 40 MHz and 60 MHz depending on the user-selectable settings. It can be appreciated that the frequency at which the ultrasound transducer emits and receives acoustic energy may vary based on the application. Some drive cables contain an electrical transmission line that electrically connects PIM 230 to the ultrasound transducer. In embodiments with mechanically rotating drive cables, the imaging element can continuously scan (rotate) through 360 degrees.

To initiate image acquisition, PIM 230 can send an electrical signal (e.g., high frequency pulse) through the transmission line to the ultrasound transducer. During "live" imaging, this high frequency pulse can be periodically and continuously sent to the transducer to excite the transducer. The transducer can convert the electrical signal into an ultrasound energy pulse or pressure wave. In some examples, the pressure wave is transmitted through an elongated imaging window of the catheter and into the adjacent vascular tissues. The vascular tissues can interact with and reflect the pressure wave back through the imaging window and onto the transducer. The transducer can convert the received ultrasound energy back into electrical energy. The electrical energy can then be transmitted, via the transmission line embedded in the drive cable, back to PIM 230 and then back to the measurement engine 210 for hemodynamic measurement.

Some examples include a telescope assembly integrated into the catheter assembly that allows the imaging of multiple regions of interest in a single procedure by advancing or retracting the imaging assembly without moving the catheter sheath. The transducer can be longitudinally translated along the imaging window by extending and collapsing the telescope assembly. This system allows for imaging along a length of an artery without moving the catheter sheath. The longitudinal translation can be performed manually by the system user or under motorized control. Motorized longitudinal translation enables the acquisition of calibrated three-dimensional volume data. This allows the measurement engine 210 to accurately measure distances along the length of the artery under investigation.

In some examples, the longitudinal translation is provided by a Linear Translation System (LTS) 220 that mates with PIM 230 and catheter assembly 240 to enable pullback of the imaging element at a controlled rate. LTS 220 can provide calibrated linear translation for measurements on the longitudinal image. LTS 220 may feature a display, which indicates the linear distance traversed and the pullback speed, as well as controls for starting/stopping pullback, setting pullback speed, resetting linear distance traversed to zero, and switching to manual mode. In manual mode, the system user can freely move the catheter imaging element forward and backward. In another example, the LTS 220 may be configured to enable either pullback and/or push-forward of the catheter imaging element at a controlled rate. In yet another example, the LTS 220 may be configured to oscillate the catheter imaging element by alternately performing pullback and push-forward operations.

In some examples, IVUS system 200 may also include an injection system 250 configured to deliver fluid into a vessel of a patient. In some examples, the injection system 250 may comprise an automated injector pump configured to deliver one or more fluids (e.g., contrast or saline) into the patient. In some examples, the automated injector pump may be in electrical communication with, and controlled by, measurement engine 210. In some examples, injection system 250 may comprise a controller configured to control the automated injector pump. In certain examples, the injection system 250 may be a manual injection pump (e.g., syringe injection) configured to allow a user to manually deliver one or more fluids into the patient. As is discussed further below, the injection system 250 may be in fluid communication with catheter assembly 240 such that fluid from the injection system is delivered into a patient's vasculature via the catheter assembly 240. As can be appreciated, the injection system 250 may be configured to deliver any number of fluids and any quantity of fluid as appropriate for a specific application of IVUS system 200.

Figure 3A:
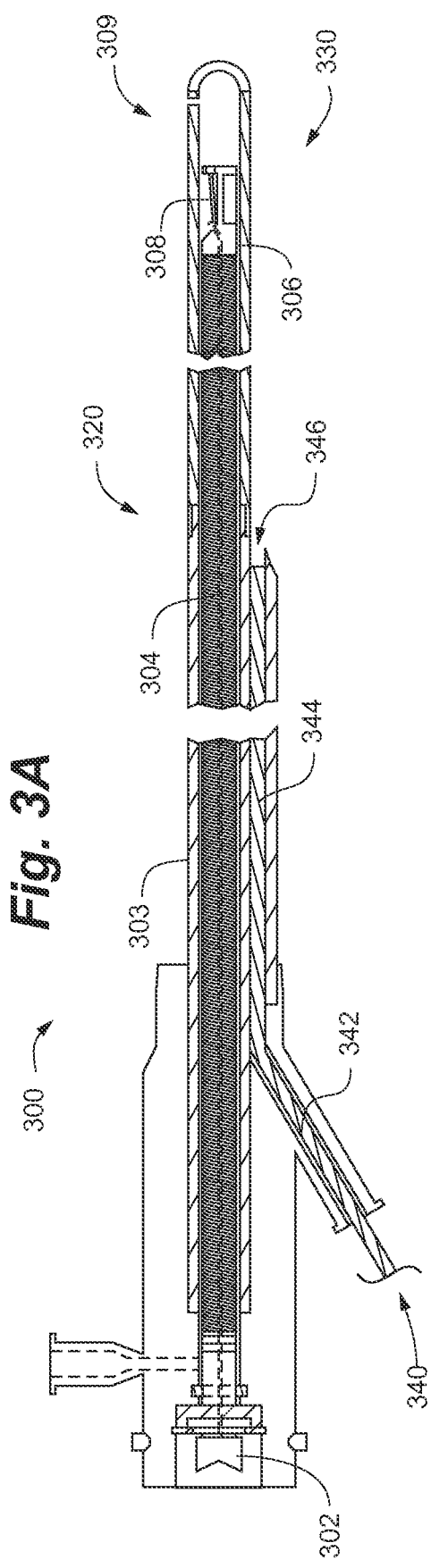
FIG. 3A is a side cross-sectional view of an illustrative catheter assembly that may be used in the IVUS system of FIG. 2.

FIG. 3A is a side cross-sectional view of a catheter assembly 300 that may be used in IVUS system 200 of FIG. 2. Referring again to FIG. 3A, as noted above, a drive cable 304 may be mechanically engaged and electrically connected to a PIM (not shown) via a connector 302. Accordingly, the PIM may be used to rotate the drive cable within sheath 303. An intravascular measuring device 309 including an ultrasound transducer 308 may be located in a distal section 330 of the catheter assembly 300. The intravascular measuring device 309 may be coupled to the drive cable such that rotation of the drive cable also causes the ultrasound transducer 308 to rotate within sheath 303. The ultrasound transducer 308 may be configured to emit and receive ultrasound energy and generate ultrasound data. In some examples, catheter assembly 300 may include an imaging window 306 substantially transparent to the frequency of the ultrasound energy emitted by ultrasound transducer 308.

In some examples, catheter assembly 300 may be in fluid communication with an injection system to deliver a quantity of fluid, or a bolus of fluid, from the injection system to a vessel of a patient. In this example, catheter assembly 300 can include an injection cannula 342 in fluid communication with the injection system upstream of point 340. The injection cannula 342 can include an injection cannula lumen 344 and an injection port 346 for delivering the fluid into the vessel. The injection system may deliver small boluses of fluid (e.g., saline or contrast dye) into the injection cannula lumen 344, out the injection port 346 and into the vessel. The injection port 346 may be located in a proximal section 320 of the catheter assembly upstream of ultrasound transducer 308 such that the injected bolus will travel with the blood flow within the vessel (i.e., left to right with reference to FIG. 3A) towards the ultrasound transducer 308. The bolus may comprise fluid that is substantially transparent to the wavelength emitted by the ultrasound transducer 308 and used as a flushing agent to clear the vessel of blood to allow for imaging of the vessel.

Figure 3B:
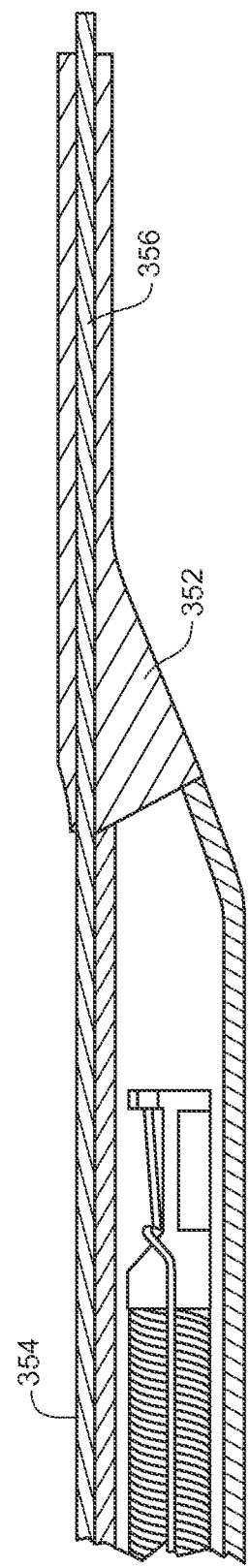
FIG. 3B is a side cross-sectional view of a distal section of an illustrative catheter assembly.

FIG. 3B is a side cross-sectional view of a distal section 350 of a catheter assembly. In some examples, distal section 350 may be used in lieu of distal section 330 included in catheter assembly 300 of FIG. 3A. Distal section 350 is similar to distal section 330 of catheter assembly 300 except that distal section 350 can include a short monorail guidewire system 351. The monorail guidewire system may include a distal end 352 forming a guidewire lumen 356 configured to accept a guidewire 354 to guide a catheter assembly into a vascular system of a patient. It can be appreciated that different examples may be configured to accept different guidewires depending on the application of the catheter assembly. In examples where a catheter is used for minimally invasive intravascular ultrasound imaging for the examination of human coronary pathology, the catheter may be a 6 F guide catheter compatible device, and the guidewire engagement system may be compatible with commercially available 0.014 in guidewires. In some examples, the monorail may include a distal radiopaque marker (not shown) in distal section 350. In some examples, the radiopaque marker may be located in distal end 352. In some examples, the distal radiopaque marker may be located 8 mm from the distal end of the catheter. In some examples, the catheter's distal tip entry profile may be <2.0 F, the catheter's crossing profile may be 3.2 F, and the catheter's working length may be 142 cm.

In some examples, systems and apparatuses discussed above may be used to perform hemodynamic measurements of a vasculature of a patient. FIG. 4 is a flow diagram illustrating a method 400 for determining a flow rate through a vessel of a patient. In some examples, method 400 may be configured to determine a velocity of blood and/or a volumetric flow rate through the vessel. Method 400 of FIG. 4 may be implemented in full or in part by a measurement engine of a measurement system. In some examples, the measurement system may be an IVUS system similar to IVUS system 200 of FIG. 2. Referring again to FIG. 4, method 400 can include delivering 410 a quantity of fluid into a vessel of a patient, generating 420 data while the quantity of fluid is in the vessel, determining 430 a travel distance of the quantity of fluid, determining 440 an elapsed time based on the data, and calculating a flow rate based on the travel distance and the elapsed time. In examples where the flow rate measured is volumetric flow, method 400 may be configured to determine 444 a physical dimension of the vessel before calculating 450 the volumetric flow rate.

For example, an injector system may deliver a bolus of fluid 410 into a vessel of a patient and an intravascular measurement device may be used to generate data 420 while the bolus is in the vessel. In some examples, a travel distance of the bolus within the vessel may be known or the data generated 420 may be used to determine the travel distance 430. In some examples, the data generated 420 may also be used to determine an elapsed time 440 during which the bolus traveled the distance. A flow rate of the vessel may then be calculated 450 based on the travel distance and the elapsed time. In examples where the flow rate is a velocity of fluid in the vessel, the flow rate may be calculated 450 using the following equation:

$$v \equiv \frac{D}{\Delta T}$$

In this example, velocity v may be calculated 450 by dividing the travel distance of the bolus within the vessel D by the elapsed time ΔT during which the bolus traveled the distance.

In some examples, the travel distance may be determined 430 based on a physical dimension of the vessel and a known volume of the quantity of fluid using the following equation:

$$D \equiv \frac{Vol}{A}$$

In this example, travel distance D may be determined by dividing the volume of the quantity of fluid Vol by a physical dimension A of the vessel. In some examples, the physical dimension may be a cross-sectional area of the vessel. In such examples, dividing the volume of the quantity of fluid by the cross-sectional area of the vessel may produce a longitudinal dimension, or a length, of the quantity of fluid. In many instances, the length of the quantity of fluid may be the travel distance D per the flow rate equation referenced above. Commonly owned U.S. patent application Ser. No. 13/834,031 ("Multiple Transducer Delivery Device and Method"), filed on Mar. 15, 2013, discusses, among other things, using an IVUS system to gather information regarding the diameter or cross-sectional area of a blood vessel and is hereby incorporated by reference herein in its entirety. In some examples, the measurement engine may be configured to automatically determine the physical dimension and the volume of the quantity of fluid and calculate travel distance D. In some examples, velocity of fluid in the vessel may be determined based on the volume of the quantity of fluid Vol, the physical dimension of the vessel A, and the elapsed time ΔT using the following equation:

$$v \equiv \frac{Vol}{A * \Delta T}$$

In examples where the flow rate is a volumetric flow rate through the vessel, the intravascular measurement device may be used to determine 444 a cross-sectional area of the vessel and the flow rate may be calculated 450 by multiplying the cross-sectional area by a velocity of fluid in the vessel.

In some examples, a measurement engine may be configured to determine a start time and/or an end time based on generated data 420 to calculate an elapsed time. For example, a measurement engine employing ultrasound technology may be configured to generate a speckle density of fluid within the vessel to determine 440 an elapsed time during which the bolus traveled the travel distance. The speckle density may be used to detect a position of the quantity of fluid within the vessel to determine a start time and/or an end time. Speckle is an image artifact that commonly appears as specks in ultrasound images that are caused when structure in an object is on a scale too small to be resolved by an imaging system. A density of speckle (e.g., the density of specks in the ultrasound image) is directly correlated to the concentration of unresolvable structure in an object. Blood may be a cause of speckle in an ultrasound image as the content of blood (e.g., red blood cells, white blood cells, platelets) is too small to be resolved by an ultrasound transducer. Generally, speckle is considered an undesirable image artifact as it can mask small but potentially diagnostically significant imaging features. To avoid speckle caused by blood, many imaging systems (e.g., IVUS, OCT) can be configured to use a flushing agent (e.g., saline, contrast, Ringer's solution, dextran, lactate solution) to clear blood out of an area of interest within a vessel before imaging the vessel. The flushing agent may be a fluid that is substantially transparent to the wavelength emitted by the ultrasound transducer.

A measurement engine may be configured to detect the position of a bolus comprising a flushing agent within a vessel based on a detection of speckle in the ultrasound data. In this example, where the measurement engine is configured to generate a speckle density, a leading edge of the bolus may be detected when the speckle density goes from high (e.g., speckle caused by blood) to low (e.g., absence of speckle in the flushing agent). Similarly, a trailing edge of the bolus may be detected when the speckle density goes from low (e.g., flushing agent) to high (e.g., blood). In some examples, one or more speckle density thresholds may be used to determine a start and/or end time corresponding to a moment where the leading or trailing edge of the bolus is detected by the ultrasound transducer. In some examples, the speckle density threshold may be predetermined and/or selected by a user. In other examples, the measurement engine may be configured to automatically determine a speckle density based on a configuration of the system and/or the specific imaging conditions of the application.

Similar methods may be used to determine the position of a bolus using imaging technologies other than IVUS. For example, the methods described above may be adapted for a measurement engine employing OCT technologies. For example, the bolus may comprise an optically transparent flushing agent. Instead of detecting a speckle density, the OCT may detect optical transparency in the vessel to determine the position of the bolus. Accordingly, in some examples, optical transparency thresholds may be used to detect the position of the bolus.

Figure 5A:
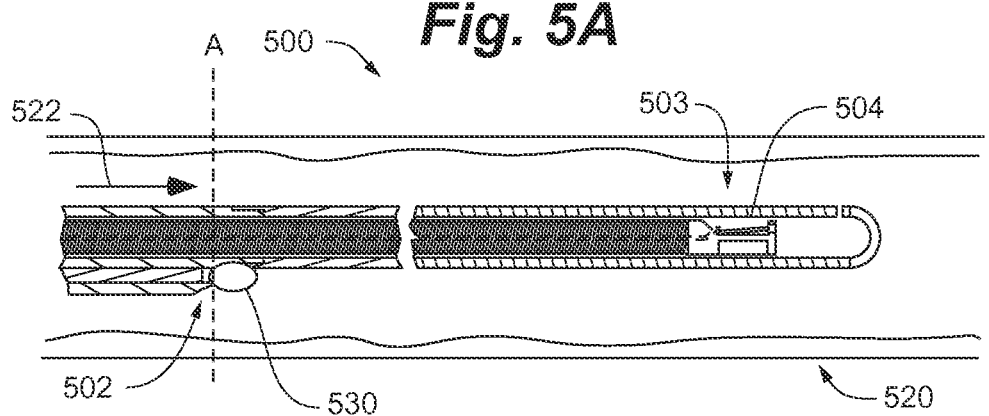
FIGS. 5A-5C are cross-sectional views of a catheter assembly within a vessel of a patient.
Figure 5B:
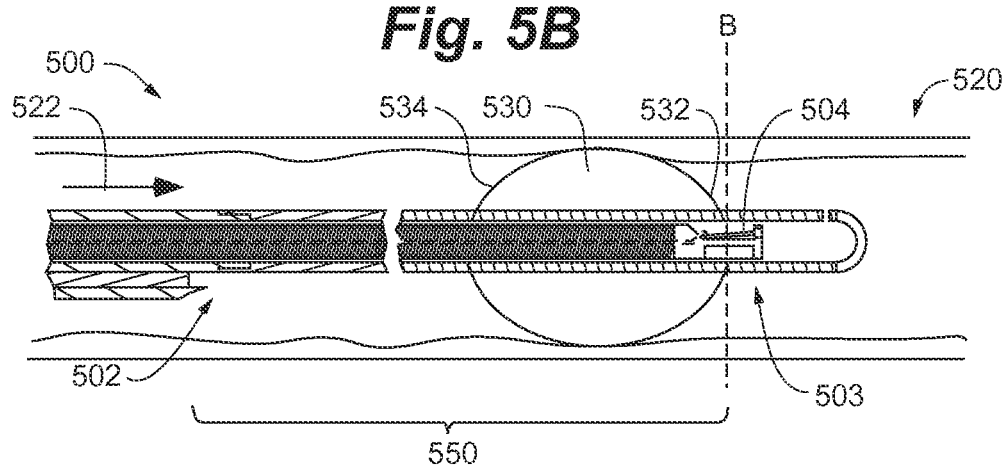
Figure 5C:
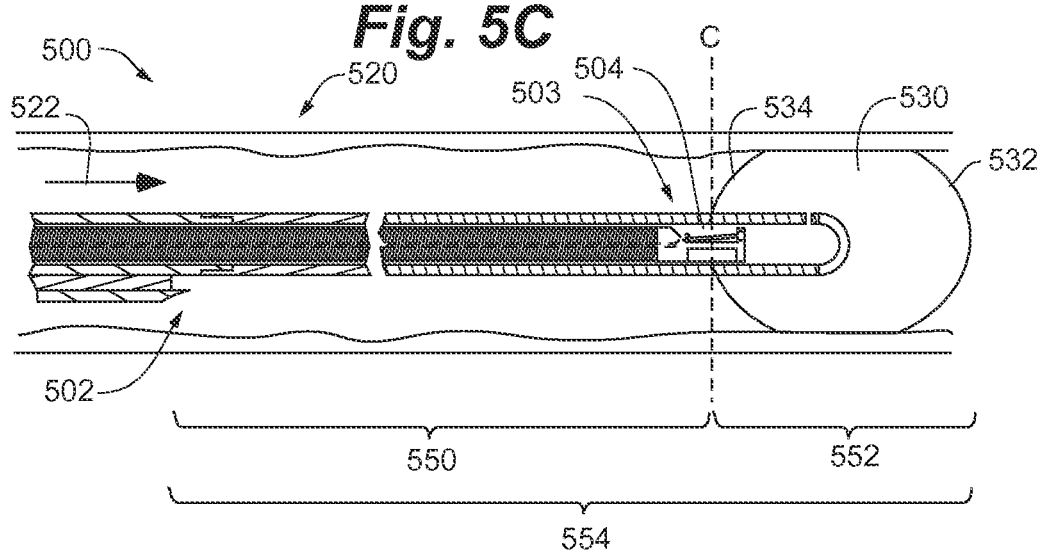

Method 400 will now be discussed in further detail with reference to FIGS. 5A-6. FIGS. 5A-5C are cross-sectional views of a catheter assembly 500 within a vessel 520 of a patient. In this example, catheter assembly 500 may include an injection port 502 and an intravascular measurement device 503 including an ultrasound transducer 504. Catheter assembly 500 may be configured to deliver a bolus of fluid into vessel 520 via injection port 502. The bolus of fluid may comprise a flushing agent. The sequence of FIGS. 5A, 5B and 5C illustrates positions of a bolus of fluid 530 within vessel 520 during and after the injection of the bolus 530 over sequential time points A, B and C, respectively. FIG.

5A corresponds with time point A, wherein bolus 530 is initially injected into vessel 520. After time point A, bolus 530 is forced by blood flow 522 towards ultrasound transducer 504. FIG. 5B corresponds with time point B, wherein a leading edge 532 of bolus 530 reaches ultrasound transducer 504. After time point C, bolus 530 continues to be forced by blood flow 522 across ultrasound transducer 504. FIG. 5C corresponds with time point C wherein a trailing edge 534 of bolus 530 reaches the ultrasound transducer. In some examples, a flow rate through a vessel may be calculated between time points A and B, between time points A and C, and/or between time points B and C.

In some examples, method 400 of FIG. 4 may be used to determine fluid flow through a vessel between time points A and B. With reference to FIG. 4 and FIGS. 5A and 5B, the bolus of fluid 530 may be delivered 410 into vessel 520 via injection port 502 of catheter assembly 500. Intravascular measurement device 503 may then image the vessel and generate 420 ultrasound data that may be received by the measurement engine. The measurement engine may be configured to determine 430 a travel distance 550 between injection port 502 and ultrasound transducer 504. In some examples, travel distance 550 may be predetermined where catheter assembly 500 is configured such that the distance between the injection port and the ultrasound transducer is fixed. In some examples, the distance between injection port 502 and ultrasound transducer 504 may vary where the catheter assembly is configured for linear translation (i.e., pullback and push forward operations). In such examples, the measurement engine may be configured to determine travel distance 550 by communicating with the linear translation system to acquire and/or calculate a physical position of the ultrasound transducer relative to the injection port.

The measurement engine may be configured to determine 440 an elapsed time during which the bolus 530 travels the travel distance 550. As noted above, the elapsed time may be calculated by determining a start time and an end time. In this example, the start time corresponds with time point A, wherein the bolus is introduced into the vessel. In examples where the measurement system includes a manual injection system (e.g., syringe), the start time may be determined and recorded by a user of the system. In some examples, the measurement engine may be in communication with the injection system such that when the bolus is delivered, the measurement engine is able to determine a time of injection. In examples where the measurement system includes an automated/synchronized injection system, the measurement engine may be configured to automatically trigger delivery of the bolus and note the time of delivery.

In this example, the end time corresponds with time point B, wherein leading edge 532 of the bolus reaches ultrasound transducer 504. As noted above, the measurement engine may be configured to generate a speckle density based on the generated 420 ultrasound data and identify leading edge 532 of the bolus based on a change in the speckle density generated. For example, ultrasound data generated in FIG. 5A at time point A may be associated with a high speckle density, because ultrasound transducer 504 is surrounded by blood. Comparatively, the ultrasound data generated in FIG. 5B at time B may be associated with a lower speckle density, as ultrasound transducer 504 is surrounded by a fluid comprising a mixture of flushing agent and blood. As noted above, in some examples, the leading edge 532 may be detected based on when the generated speckle density crosses a predetermined speckle density threshold from high (e.g., blood) to low (e.g., flushing agent). Accordingly, the end time, or in this example, time point B, is when the speckle density crosses the predetermined speckle density threshold from high to low. The elapsed time may then be determined 440 by calculating the time between the start time and the end time. The flow rate through the vessel between time point A and time point B may then be calculated 450 by dividing the travel distance 550 by the elapsed time.

In some examples, method 400 of FIG. 4 may be used to determine a flow through a vessel between time points B and C. With reference to FIG. 4 and FIGS. 5B and 5C, the bolus of fluid 530 may be delivered 410 and data may be generated 420 using steps similar to the steps described above with regard to determining fluid flow between time points A and B. In this example, however, the start time may correspond with time point B wherein leading edge 532 reaches ultrasound transducer 504, and the end time may correspond with time point C wherein trailing edge 534 reaches the ultrasound transducer. In some examples, leading edge 532 may be detected based on when the generated speckle density crosses a predetermined speckle density threshold from high (e.g., blood) to low (e.g., flushing agent), and the start time may be determined based on when the leading edge is detected. Similarly, trailing edge 534 may be detected based on when the generated speckle density crosses a predetermined speckle density threshold from low (e.g., flushing agent) to high (e.g., blood), and the end time may be determined based on when the trailing edge is detected. In some examples, a first predetermined speckle density threshold may be used to determine the start time and a second predetermined speckle density threshold may be used to determine the end time.

Further, in this example travel distance 552 corresponds with a longitudinal dimension, or a length, of the bolus of fluid and may be determined 430 based on a physical dimension of the vessel (e.g., cross-sectional area of the vessel) and a known volume of the bolus of fluid. As described above, the measurement engine may be configured to calculate a cross-sectional area or a diameter of the vessel. Further, the measurement engine may be configured to automatically determine and/or measure the volume of the bolus injected into the vessel. Travel distance 552 may be determined based on the known volume of the bolus of fluid and the cross-sectional area of the vessel. In some embodiments, travel distance 552 can be the volume of the bolus 530 divided by the cross-sectional area of the vessel 520, as that entire length of bolus 530 will have traveled past ultrasound transducer 540 between time point B and time point C. Accordingly, the flow rate through the vessel between time point B and time point C may be calculated 450 by dividing travel distance 552 by the elapsed time. In some instances, the flow rate may be calculated 450 by dividing the known volume of fluid by the product of the cross-sectional area of the vessel and the elapsed time.

In some examples, method 400 of FIG. 4 may be used to determine fluid flow through a vessel between time points A and C. With reference to FIG. 4 and FIGS. 5A and 5C, the bolus of fluid 530 may be delivered 410 and data may be generated 420 using steps similar to the steps described above with regard to determining fluid flow between time points A and B, and also time points B and C. Travel distance 554 of bolus 530 is equal to the sum of travel distance 550 and travel distance 552. Travel distance 550 and travel distance 552 may be determined using the steps described above with regard to determining fluid flow between time points A and B, and between time points B and C, respectively. In this example, the elapsed time may be determined 440 based on an end time corresponding with time point C wherein trailing edge 534 of bolus 530 reaches ultrasound transducer 504. In some examples, trailing edge 534 may be detected based on when the generated speckle density crosses a predetermined speckle density threshold from low (e.g., flushing agent) to high (e.g., blood). Accordingly, the end time, or in this example time point C, is when the speckle density crosses the predetermined speckle density threshold from low to high. As is discussed further below, it should be appreciated that fluid turbulence and/or recirculation of blood in a vessel may cause variance in the shape of leading edge 532 as compared to trailing edge 534 of the bolus 530 and therefore different predetermined speckle density thresholds may be used depending on whether fluid flow is measured between time points A and B or time points A and C.

In some examples, a measurement engine may be configured to calculate multiple flow rates using one or all of the examples described above. For example, a measurement engine may be configured to calculate the flow rates between time points A and B, A and C, and B and C. The multiple flow rates calculated may be averaged to even out potential error, or compared to eliminate outlying results.

Figure 6:
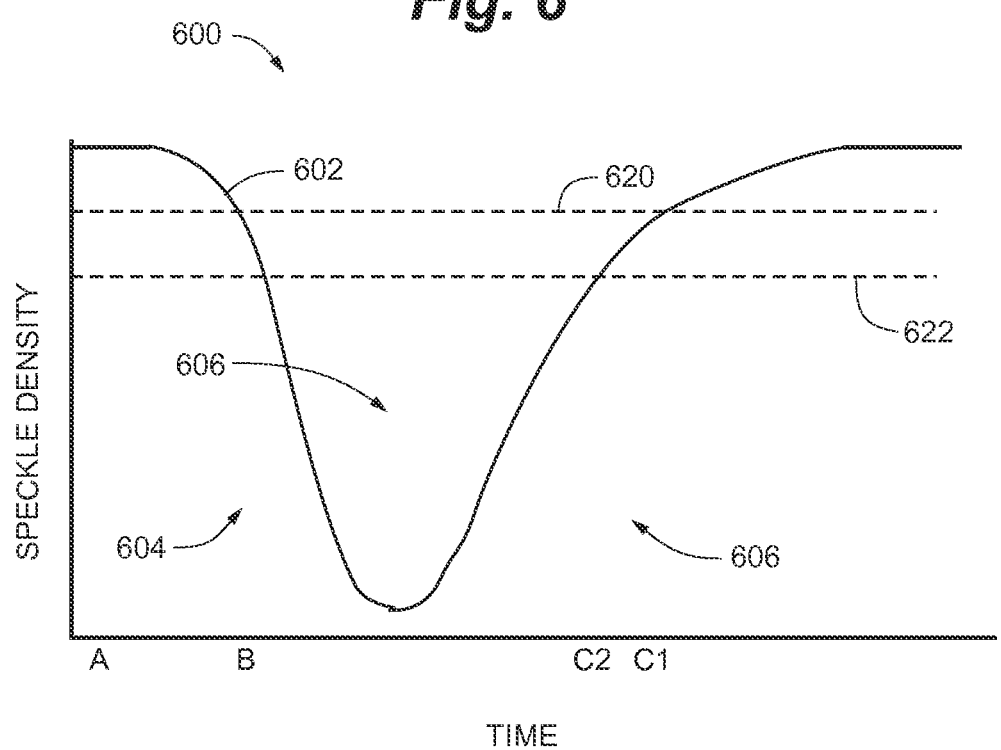
FIG. 6 is a plot of speckle density generated by a measurement engine over time.

FIG. 6 is a plot 600 of speckle density 602 generated by a measurement engine over time. With reference to FIG. 6 and FIGS. 5A-5C, plot 600 includes time points A and B which correspond to FIGS. 5A and 5B, respectively, and time points C1 and C2 which correspond with FIG. 5C. Speckle density 602 includes a first portion 604 corresponding to leading edge 532 of bolus 530, and a second portion 606 corresponding to a trailing edge 534 of the bolus. Plot 600 also includes first and second predetermined speckle density thresholds 620 and 622, respectively, which may be used alone or in combination to determine when leading edge 532 and trailing edge 534 reach ultrasound transducer 504.

In this example, time point A corresponds with an initial injection of bolus of fluid 530 into vessel 520. At that time, ultrasound transducer 504 is surrounded by blood, and the speckle density 602 at time point A is high. As illustrated in plot 600, as leading edge 532 of the bolus nears the ultrasound transducer 504, the transducer is surrounded by a mixture of blood and flushing agent. Accordingly, the speckle density 602 continues to decrease as the leading edge of the bolus 530 nears the ultrasound transducer 504. In this example, a measurement engine may determine that the leading edge of the bolus 530 has reached ultrasound transducer 504 at time point B when speckle density 602 crosses first predetermined speckle density threshold 620 from high to low. Similarly, in some examples, the measurement engine may determine that trailing edge 534 of bolus 530 has reached the ultrasound transducer at time point C1 when speckle density 602 crosses first predetermined speckle density threshold 620 from low to high.

In some examples, a measurement engine may be configured to use more than one predetermined speckle density threshold. For example, a measurement engine may be configured to use first and second predetermined speckle density thresholds 620 and 622 to determine when a leading edge of a bolus and a trailing edge of a bolus have reached the ultrasound transducer 504, respectively. Accordingly, a measurement engine may determine that trailing edge 534 of bolus 530 crosses the ultrasound transducer at time point C2 when speckle density 602 crosses the second predetermined speckle density threshold from low to high. The use of more than one predetermined speckle density thresholds may be advantageous where there is recirculation of blood in the vessel that may cause variance between the leading edge and the trailing edge of the bolus.

Figure 7A:
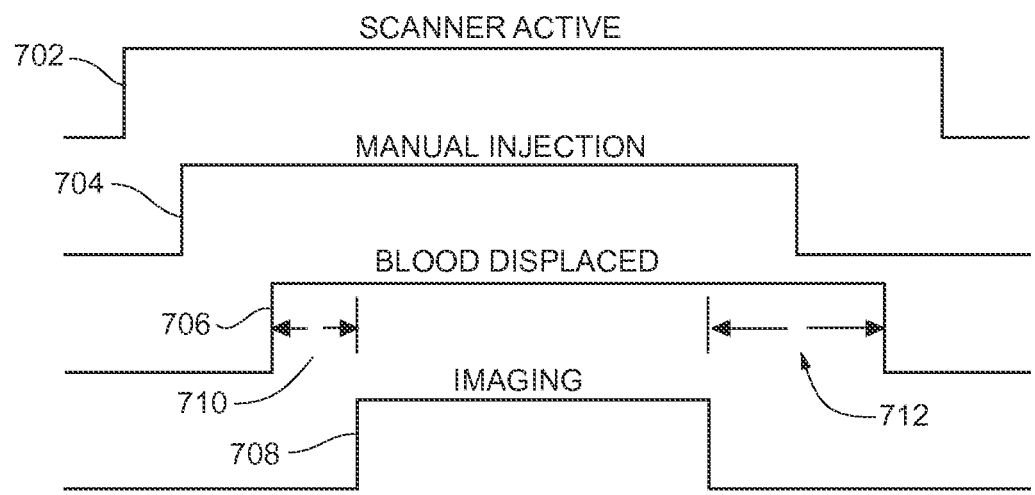
FIG. 7A illustrates a technique for manually clearing blood from a vessel for imaging.

In some examples, a measurement system may include a measurement engine in communication with, and/or synchronized to, an injection system. As noted above, fluid delivered into a vessel of a patient may displace the blood within the vessel. In many instances, it may be beneficial to minimize the amount of fluid injected in order to reduce the amount of time the fluid displaces blood within the vessel. Prolonged periods of blood displacement may cause anoxic episodes, which may stress tissue downstream of the displacement. FIG. 7A illustrates a common method for manually clearing blood from an area of interest within a vessel and imaging the area of interest using the measurement engine. In step 702, the measurement engine may begin scanning. In step 704, fluid may be manually injected into the vessel to displace the blood within the area of interest. After the blood has been displaced, a user may begin imaging the area of interest using the measurement engine in step 708.

As shown in FIG. 7A, user delay may cause blood to be displaced from the vessel for longer than necessary to perform the imaging of the area of interest as the user may not immediately begin imaging in step 708 as soon as blood is displaced. Further, the user may not deactivate the manual injection to cease displacement of the blood immediately after the imaging is complete. Consequently, for a period of time 710 before imaging is commenced, and for a period of time 712 after imaging is completed, blood is needlessly displaced from the vessel without providing any benefit to the quality of the image.

Figure 7B:
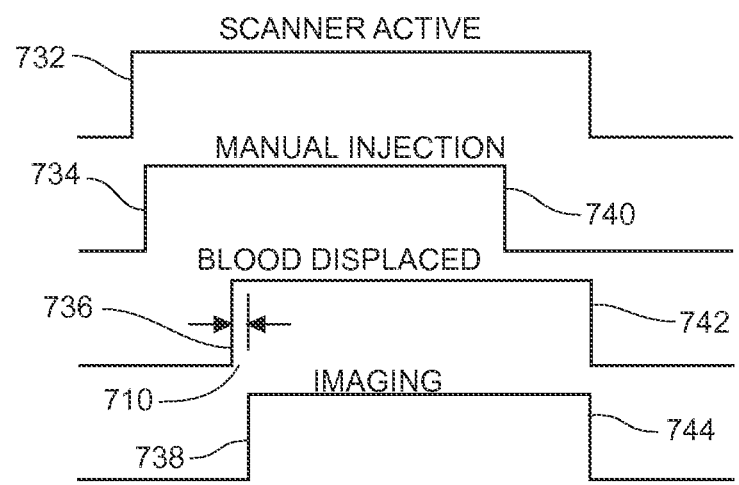
FIG. 7B illustrates a technique for automatically clearing blood from a vessel for imaging.

FIG. 7B illustrates an example where blood displacement is minimized during imaging. In this example, a measurement engine may be in communication and/or synchronized with an injection system. As shown in FIG. 7B, the measurement engine may begin scanning in step 732 and fluid may be automatically injected into the vessel in step 734 to displace the blood within the vessel. In some examples, in order to account for any delay between triggering an injection and the fluid actually clearing the vessel, the measurement engine may be configured to delay imaging. The period of delay may be the length of time it takes for fluid to travel from the injection system to the area of interest. After the delay, the measurement engine may begin imaging the area of interest in step 738. When properly synchronized, the measurement engine will begin imaging immediately after blood is displaced from the vessel. As illustrated, time period 710, wherein blood is displaced and no imaging is taking place, may be substantially reduced. A similar delay may also be used at the tail end of imaging. For example, the injection system may be configured to cease delivery of the fluid in step 740 before the measurement engine ceases imaging. After a predetermined delay, the measurement engine may cease imaging in step 744. When properly synchronized, the measurement engine will cease imaging immediately before blood returns to the area of interest.

In some examples, the measurement engine may be configured to trigger the injection system to automatically deliver the fluid. In some examples, the measurement engine may be configured to communicate to the injection system to stop delivery of the fluid.

Other advantages to communication between, and/or synchronization of, the measurement engine with the injection system may include higher measurement accuracy of fluid flow through a vessel. For example, a start time may be more accurately determined based on synchronization and/or communication between the measurement engine and the injection system as compared to the use of a manual injection system. As blood flow may reach speeds up to 1 meter per second in the vasculature of a patient, any delay in recording the start time may introduce significant error into the fluid flow measurement. In some examples, a measurement engine may be synchronized with an injection system to automatically disable image filtering functionality during measurement operations. For example, many IVUS imaging systems include filtering functionality to reduce image artifacts caused by speckle in an ultrasound image. Reduction of speckle, while advantageous for imaging, reduces the speckle density contrast between that of blood and a flushing agent and may inhibit the detection of the leading and trailing edges of a bolus. Thus, higher measurement accuracy may be achieved in a system where the measurement engine is synchronized, and/or in communication, with a the injection system.

One skilled in the art will appreciate that the techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

Further, the techniques described in this disclosure may also be embodied or encoded in a non-transitory computer-readable medium, such as a computer-readable storage medium, containing instructions. Instructions embedded or encoded in a computer-readable storage medium may cause a programmable processor, or other processor, to perform the method, e.g., when the instructions are executed. Non-transitory computer readable storage media may include volatile and/or non-volatile memory forms including, e.g., random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples of the invention have been described. Although the present invention has been described in considerable detail with reference to certain disclosed embodiments, the embodiments are presented for purposes of illustration and not limitation. Other embodiments incorporating the invention are possible. One skilled in the art will appreciate that various changes, adaptations, and modifications may be made without departing from the spirit of the invention and the scope of the appended claims.

What is claimed is:

1. A system comprising:
a catheter assembly including an intravascular measuring device comprising an intravascular ultrasound imaging probe having a measurement module configured to emit and receive energy and generate ultrasound measurement data, the catheter assembly configured to introduce a quantity of fluid into a vessel of a patient; and
a measurement engine in communication with the intravascular measuring device comprising at least one processor, the measurement engine configured to:
receive the ultrasound measurement data from the intravascular measuring device;
generate, using the at least one processor, a speckle density value based on the ultrasound measurement data, the speckle density value corresponding to a concentration of structure in the vessel that is too small to be resolved by the intravascular ultrasound imaging probe, wherein when the quantity of fluid is introduced into the vessel the speckle density value is relatively high compared to the speckle density value when the intravascular ultrasound imaging probe is surrounded by the quantity of fluid;
determine a fluid flow travel start time associated with an introduction of the quantity of fluid into a predetermined portion of the vessel;
determine a fluid flow travel end time as being when the speckle density crosses a first predetermined speckle density threshold using the at least one processor;
calculate, using the at least one processor, an elapsed fluid flow travel time based on the fluid flow travel start time and the fluid flow travel end time; and
calculate, using the at least one processor, a flow rate of the quantity of fluid through the vessel based on the elapsed fluid flow travel time and a travel distance of the quantity of fluid during the elapsed fluid flow travel time.

2. The system of claim 1, wherein the measurement engine is configured to calculate the flow rate by dividing the travel distance of the quantity of fluid during the elapsed fluid flow travel time by the elapsed fluid flow travel time.

3. The system of claim 1, wherein the fluid flow travel start time is when the quantity of fluid is introduced into the vessel.

4. The system of claim 1, wherein the fluid flow travel end time is when the speckle density crosses the first predetermined speckle density threshold from a higher speckle density to a lower speckle density.

5. The system of claim 1, wherein the fluid flow travel end time is when the speckle density crosses the first predetermined speckle density threshold from a lower speckle density to a higher speckle density.

6. The system of claim 1, wherein the fluid flow travel start time is when the speckle density crosses a second predetermined speckle density threshold from a first higher speckle density to a first lower speckle density, and the fluid flow travel end time is when the speckle density crosses the first predetermined speckle density threshold from a second lower speckle density to a second higher speckle density.

7. The system of claim 1, wherein the measurement engine is configured to determine the travel distance of the quantity of fluid during the elapsed fluid flow travel time based on a distance between where the quantity of fluid is introduced into the vessel of the patient and where the measurement module is located.

8. The system of claim 1, wherein the quantity of fluid comprises a contrast media.

9. The system of claim 1, wherein the quantity of fluid comprises a saline solution.

10. The system of claim 1, wherein the intravascular measuring device is configured to emit and receive ultrasound energy at a frequency greater than or equal to 40 MHz.

11. The system of claim 1, further comprising an injection system configured to deliver the quantity of fluid into the vessel of the patient, wherein the measurement engine is configured to automatically measure fluid flow in the vessel of the patient in response a delivery of the quantity of fluid by the injection system.

12. The system of claim 1, wherein the quantity of fluid comprises a flushing agent.

13. The system of claim 1, wherein the measurement engine is further configured to determine, using the at least one processor, a physical dimension of the vessel based on the ultrasound measurement data and to calculate the flow rate based on the physical dimension of the vessel.

14. The system of claim 13, wherein the physical dimension comprises a cross-sectional area of the vessel.

15. The system of claim 14, wherein the measurement engine is configured to determine the travel distance of the quantity of fluid during the elapsed fluid flow travel time based on a known volume of the quantity of fluid and the cross-sectional area of the vessel.

16. The system of claim 14, wherein the measurement engine is configured to calculate the flow rate by multiplying the cross-sectional area of the vessel and a quotient of the travel distance of the quantity of fluid during the elapsed fluid flow travel time and the elapsed fluid flow travel time.

17. A non-transitory computer-readable storage article comprising computer-executable instructions stored thereon to cause at least one programmable processor to:
receive ultrasound measurement data of a vessel of a patient acquired by an intravascular measuring device comprising an intravascular ultrasound imaging probe having a measurement module;
generate a speckle density value based on the ultrasound measurement data, the speckle density value corresponding to a concentration of structure in the vessel that is too small to be resolved by the intravascular ultrasound imaging probe;
determine a fluid flow travel start time associated with an introduction of a quantity of fluid into a predetermined portion of the vessel, wherein when the quantity of fluid is introduced into the vessel the speckle density value is relatively high compared to the speckle density value when the intravascular ultrasound imaging probe is surrounded by the quantity of fluid;
determine a fluid flow travel end time as being when the speckle density crosses a first predetermined speckle density threshold;
calculate an elapsed fluid flow travel time based on the fluid flow travel start time and the fluid flow travel end time; and
calculate a flow rate of the quantity of fluid through the vessel based on the elapsed fluid flow travel time and a travel distance of the quantity of fluid during the elapsed fluid flow travel time.

18. The article of claim 17, wherein the flow rate is calculated by dividing the travel distance of the quantity of fluid during the elapsed fluid flow travel time by the elapsed fluid flow travel time.

19. The article of claim 17, wherein the fluid flow travel start time is when the quantity of fluid is introduced into the vessel.

20. The article of claim 17, wherein the fluid flow travel end time is when the speckle density crosses the first predetermined speckle density threshold from a higher speckle density to a lower speckle density.

21. The article of claim 17, wherein the fluid flow travel end time is when the speckle density crosses the first predetermined speckle density threshold from a lower speckle density to a higher speckle density.

22. The article of claim 17, wherein the fluid flow travel start time is when the speckle density crosses a second predetermined speckle density threshold from a first higher speckle density to a first lower speckle density, and wherein the fluid flow travel end time is when the speckle density crosses the first predetermined speckle density threshold from a lower speckle density to a higher speckle density.

23. The article of claim 17, further comprising executable instructions to cause the at least one programmable processor to determine the travel distance of the quantity of fluid during the elapsed fluid flow travel time based on a distance between where the quantity of fluid is introduced into the vessel of the patient and where the measurement module is located.

24. The article of claim 17, wherein the intravascular measuring device emits and receives ultrasound energy at a frequency greater than or equal to 40 MHz.

25. The article of claim 17, further comprising executable instructions to cause the at least one programmable processor to determine a physical dimension of the vessel based on the ultrasound measurement data and to calculate the flow rate based on the physical dimension of the vessel.

26. The article of claim 25, wherein the physical dimension comprises a cross-sectional area of the vessel.

27. The article of claim 26, further comprising executable instructions to cause the at least one programmable processor to determine the travel distance of the quantity of fluid during the elapsed fluid flow travel time based on a known volume of the quantity of fluid and the cross-sectional area of the vessel.

28. The article of claim 26, wherein the flow rate is calculated by multiplying the cross-sectional area of the vessel and a quotient of the travel distance of the quantity of fluid during the elapsed fluid flow travel time and the elapsed fluid flow travel time.

* * * * *